US012746316B2

(12) United States Patent
Bozzay

(10) Patent No.: US 12,746,316 B2
(45) Date of Patent: Sep. 29, 2026

(54) SYSTEMS, ASSEMBLIES, AND METHODS OF TRAUMA MANAGEMENT

(71) Applicant: Lazarus Technologies LLC, Nolensville, TN (US)

(72) Inventor: Tom Bozzay, Little Rock, AR (US)

(73) Assignee: Lazarus Technologies LLC, Nolensville, TN (US)

(*) Notice: Subject to any disclaimer, the term of this patent is extended or adjusted under 35 U.S.C. 154(b) by 313 days.

(21) Appl. No.: 18/648,021

(22) Filed: Apr. 26, 2024

(65) Prior Publication Data

US 2025/0082834 A1 Mar. 13, 2025

Related U.S. Application Data

(62) Division of application No. 18/381,948, filed on Oct. 19, 2023, now Pat. No. 11,998,675.

(Continued)

(51) Int. Cl.

*A61M 1/36* (2006.01)
*A61M 1/16* (2006.01)

(52) U.S. Cl.

CPC ........ *A61M 1/3639* (2013.01); *A61M 1/1698* (2013.01); *A61M 1/3603* (2014.02); *A61M 1/36225* (2022.05); *A61M 1/362263* (2022.05); *A61M 1/362265* (2022.05); *A61M 1/362266* (2022.05); *A61M 1/3623* (2022.05); *A61M 1/3624* (2013.01); *A61M 1/365* (2014.02); *A61M 1/367* (2013.01); *A61M 2202/0021* (2013.01); *A61M 2202/0208* (2013.01); *A61M 2202/0225* (2013.01); *A61M 2202/0413* (2013.01); *A61M 2205/103* (2013.01); *A61M 2205/3303* (2013.01);

(Continued)

(58) Field of Classification Search

None

See application file for complete search history.

(56) References Cited

U.S. PATENT DOCUMENTS

| | | | | |
|---|---|---|---|---|
| 12,447,177 | B2 * | 10/2025 | Dunham ................ | A61K 35/14 |
| 2008/0294252 | A1 | 11/2008 | Myklebust | |

(Continued)

FOREIGN PATENT DOCUMENTS

| | | | | |
|---|---|---|---|---|
| WO | WO-2022040376 | A2 * | 2/2022 | .......... A61M 1/1696 |

OTHER PUBLICATIONS

U.S. Appl. No. 18/381,948, 312 Amendment filed Mar. 18, 2024, 7 pgs.

(Continued)

*Primary Examiner* — Leslie R Deak
*Assistant Examiner* — Linnae E. Raymond
(74) *Attorney, Agent, or Firm* — Schwegman, Lundberg & Woessner, P.A.

(57) ABSTRACT

A system for performing extracorporeal blood treatment of recovered blood can include a reservoir to receive a first portion of the recovered blood from a subject, an inline pump coupled the reservoir to regulate a flow rate of at least the first portion of the recovered blood, and an extracorporeal blood conditioner including at least one of an oxygenator to reoxygenate hemoglobin included in the recovered blood for at least intravenous delivery back to the subject or a temperature regulator configured to selectively control a temperature of the recovered blood.

11 Claims, 11 Drawing Sheets

Related U.S. Application Data

(60) Provisional application No. 63/417,574, filed on Oct. 19, 2022.

(52) U.S. Cl.
CPC ............... *A61M 2205/3327* (2013.01); *A61M 2205/3334* (2013.01); *A61M 2205/3368* (2013.01); *A61M 2205/3606* (2013.01); *A61M 2205/3673* (2013.01); *A61M 2205/50* (2013.01); *A61M 2205/7545* (2013.01); *A61M 2205/8206* (2013.01); *A61M 2209/088* (2013.01); *A61M 2230/20* (2013.01); *A61M 2230/50* (2013.01)

(56) References Cited

U.S. PATENT DOCUMENTS

| | | | | |
|---|---|---|---|---|
| 2009/0043212 | A1* | 2/2009 | Ranucci | A61B 5/742 600/484 |
| 2009/0320684 | A1 | 12/2009 | Weaver et al. | |
| 2011/0315611 | A1 | 12/2011 | Fulkerson et al. | |
| 2012/0172781 | A1 | 7/2012 | Wang | |
| 2012/0189711 | A1 | 7/2012 | Greenberg et al. | |
| 2012/0203158 | A1* | 8/2012 | Beyersdorf | A61M 5/1408 604/4.01 |
| 2013/0220907 | A1 | 8/2013 | Fulkerson et al. | |
| 2014/0276371 | A1 | 9/2014 | Updyke et al. | |
| 2017/0102846 | A1 | 4/2017 | Ebler et al. | |
| 2017/0128637 | A1 | 5/2017 | Mann et al. | |
| 2017/0333685 | A1 | 11/2017 | Kassab et al. | |
| 2019/0175813 | A1* | 6/2019 | Spearman | A61M 1/3607 |
| 2022/0249756 | A1 | 8/2022 | Chawla | |
| 2024/0131243 | A1 | 4/2024 | Bozzay | |

OTHER PUBLICATIONS

U.S. Appl. No. 18/381,948, Notice of Allowance mailed Mar. 4, 2024, 13 pgs.

U.S. Appl. No. 18/381,948, PTO Response to Rule 312 Communication mailed Mar. 29, 2024, 2 pgs.

U.S. Appl. No. 18/381,948, Response filed Feb. 13, 2024 to Restriction Requirement mailed Feb. 1, 2024, 9 pgs.

U.S. Appl. No. 18/381,948, Restriction Requirement mailed Feb. 1, 2024, 6 pgs.

U.S. Appl. No. 18/381,948, Supplemental Amendment filed Feb. 22, 2024, 10 pgs.

International Application Serial No. PCT/US2023/035517, International Search Report mailed Apr. 12, 2024, 2 pgs.

International Application Serial No. PCT/US2023/035517, Written Opinion mailed Apr. 12, 2024, 6 pgs.

Kiser, Kelsie A., et al., "Extensive Cell Salvage and Postoperative Outcomes Following Thoracoabdominal and Descending Aortic Repair", The Journal of Thoracic and Cardiovascular Surgery, vol. 163, Issue 3, (Mar. 2022).

Patel, Surendra, et al., "Use of roller pump in venovenous extracorporeal membrane oxygenation as an emergency rescue procedure", Indian Journal of Thoracic and Cardiovascular Surgery, (Aug. 31, 2022), 8 pgs.

* cited by examiner

SYSTEMS, ASSEMBLIES, AND METHODS OF TRAUMA MANAGEMENT

CLAIM OF PRIORITY

This application is a divisional of U.S. patent application Ser. No. 18/381,948, filed Oct. 19, 2023, which claims priority to U.S. Provisional Application Ser. No. 63/417,574, filed on Oct. 19, 2022, which is incorporated by reference herein in its entirety, and the benefit of priority of each of which is claimed herein.

BACKGROUND

Severe blood loss of a trauma patient can cause irreversible damage to vital organs that can lead to morbidity or death. Replacement of lost tissue fluid with plasma, blood, or other extracellular fluid can be performed in an attempt to maintain the patient's blood pressure. Generally, a trauma treatment protocol can involve rapid transportation of the patient to a hospital setting for fluid resuscitation, blood transfusion, or surgical control of bleeding. Once the patient has lost a significant amount of tissue fluid, prevention of hemorrhagic shock can become a primary concern.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

Figure 1A:
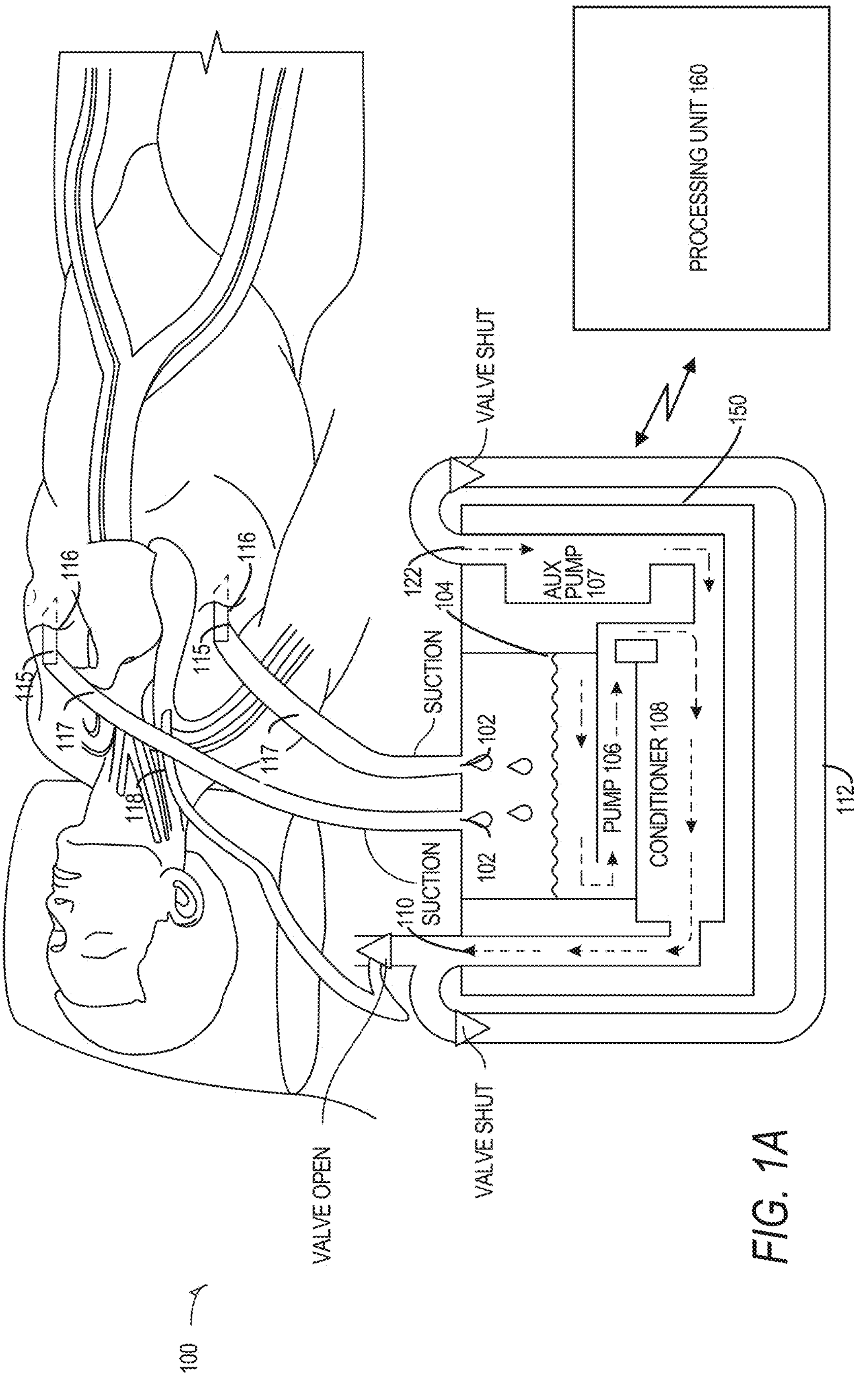
FIG. 1A depicts an example of a system for performing extracorporeal blood treatment of blood recovered from a subject.

This document relates to treatment of a trauma victim, and more specifically, blood treatment to mitigate coagulopathy, hypothermia, or acidosis of the trauma patient. Generally, hemorrhagic shock is a common cause of death among trauma patients. This condition occurs when severe blood loss leads to inadequate tissue perfusion, causing a decrease in oxygen and nutrient delivery to vital organs. As a result, the body enters a state of shock and can quickly lead to multi-organ failure and death. In severe trauma cases, such as from a gunshot wound or motor vehicle accident, the body can quickly lose a significant amount of blood volume, complicating the body's ability to maintain normal blood function.

Coagulopathy, hypothermia, and acidosis are interrelated factors that can lead to hemorrhagic shock. Coagulopathy is an imbalance between the body's pro-coagulant pathway, responsible for clot formation at the injury site, and the mechanisms that inhibit clotting away from the injury site. As the body loses blood in a trauma situation, blood flow is decreased causing hypoperfusion. Hypoperfusion results in a simultaneous lack of clotting factor replacement at the wound site (hemorrhage) and an increase in clotting in the extremities (thrombosis), both of which can cause damage to extremities and organs. Trauma Induced Coagulopathy (TIC), is an impairment of hemostasis and activation of fibrinolysis that occurs early after injury and is biochemically evident prior to, and independent of, the development of significant acidosis, hypothermia, or hemodilution. The risk of TIC increases with hypotension, higher injury severity score, worsening base deficit, and head injury. In addition, impaired liver function due to shock can also contribute to coagulopathy as the liver is responsible for producing many of the clotting factors. Hypothermia is a decrease in body temperature, which can also result from blood loss, and can further impair the body's ability to maintain normal blood function. Acidosis, referring to an abnormal increase in acidity in the body, can also result from inadequate tissue perfusion and impair the body's ability to regulate blood function. These three conditions can exacerbate one another, creating a positive feedback loop leading to severe shock and eventually death if not promptly addressed. For example, disseminated intravascular coagulation (DIC) is a systemic process producing a consumptive coagulopathy in concert with diffuse microvascular thrombosis. DIC can increase acidosis through the production of lactic acid and can also worsen hypothermia by impairing blood flow to vital organs. Hypothermia can further worsen coagulopathy, since enzymes and proteins for forming clots become less active and less effective at lower temperatures. Acidosis can also contribute to coagulopathy since the body's normal clotting processes are disrupted and become less effective at lower pH levels. Also, acidosis can further decrease body temperature, exacerbating the effects of hypothermia.

One approach to mitigating these factors and improving outcomes for trauma patients is to administer blood components, such as plasma, platelets, or red blood cells in an attempt to provide nutrients and support for the body to maintain blood functions. Such treatment involves early and aggressive treatment of a trauma patient in an attempt to restore and maintain adequate blood volume until the patient can undergo surgery or other recovery procedure. This approach can be challenging, as such treatment alone may not sufficiently address coagulopathy, hypothermia, and acidosis, particularly in severe trauma cases. For example, administering large amounts of blood products can further contribute to coagulopathy or lead to additional complications, such as fluid overload. Additionally, the use of blood products can be limited by availability, time constraints, or potential incompatibilities. Even the largest healthcare facilities can quickly become depleted of blood units in response to a large crisis, e.g., resulting from terrorism, violent crime, or natural disaster. Such crises can result in preventable deaths due to blood shortages or a lack of sufficient resources to treat the large number of trauma patients requiring immediate medical attention.

Another approach for improving outcomes for trauma patients involves administering clotting agents, such as tranexamic acid or a similar agent, to help minimize bleeding and promote clot formation. As a result, clotting agents alone will not sufficiently mitigate coagulopathy to prevent progression to severe shock but worsen shock if given at an inappropriate time. However, clotting agents at the inappropriate time can worsen coagulopathy, such as the location of the clotting. Appropriate timing for clot formation after repairing injured vessels is paramount following injury. Due to the consumptive nature of DIC, the patient's injury site where repaired vessels and grafts are sewn into place leads to poor clotting because these suture sites usually are larger vessels (higher blood flow) and micro clotting in the smaller vessels due to hypoperfusion (lower blood flow) causing decreased oxygen to the tissue and furthering acidosis. Clotting agents do not address hypothermia and acidosis, which can further impair the body's normal clotting processes.

The present inventor has recognized a need for a technique to treat or preserve a trauma patient without relying on ideal or preferred treatment conditions, e.g., availability of externally sourced blood components or rapid transportation of the patient to a large medical facility. Further, the present inventor has recognized a blood treatment technique for intervening in an initial blood treatment protocol, such as limiting tissue damage of a patient rapidly approaching hemorrhagic shock. Such an intervention can help delay the onset of cell death (necrosis) in trauma patients with a declining condition, such as providing the patient with more time to receive definitive medical treatment. A method for trauma management can include drawing blood from a body cavity, such as an intrathoracic or intra-abdominal area, of a subject via a fluid inlet of a blood treatment device. The drawn blood can be received within the device's reservoir and pumped toward an extracorporeal blood conditioner. For example, the extracorporeal blood conditioner can include an oxygenator for reoxygenating hemoglobin (Hb) or removing carbon dioxide $CO_2$ included in the blood received from the reservoir. Also, the extracorporeal blood conditioner can include a blood temperature regulator for controlling the temperature of the blood received from the reservoir. The treated blood from at least one extracorporeal blood conditioner can be administered back to the subject, such as to help replace lost blood volume in the subject. For example, the treated blood can be intravenously administered back to the subject via the subject's internal jugular vein. An indication of a blood parameter such as volume of received blood, blood lactate, or arterial blood gas (ABG) can be monitored, and at least one operating parameter of the extracorporeal blood conditioner can be established or adjusted based on the indication. For example, the device can regulate oxygenation, flow rate, or blood temperature according to different operating modes, and an individual operating mode can be selected based on the medical condition of a subject. In operation and use, an anticoagulant can be administered to induce an anti-clotting state, and the device can be operated according to a series of modes, each mode progressively corresponding with a declining subject's medical condition. Thus, such a blood treatment technique can help monitor and inhibit coagulopathy (at least via the anticoagulant), acidosis (at least via the oxygenator), and hypothermia (at least via the blood temperature regulator) of the subject and, therefore, reduce hemorrhagic shock.

Figure 1B:
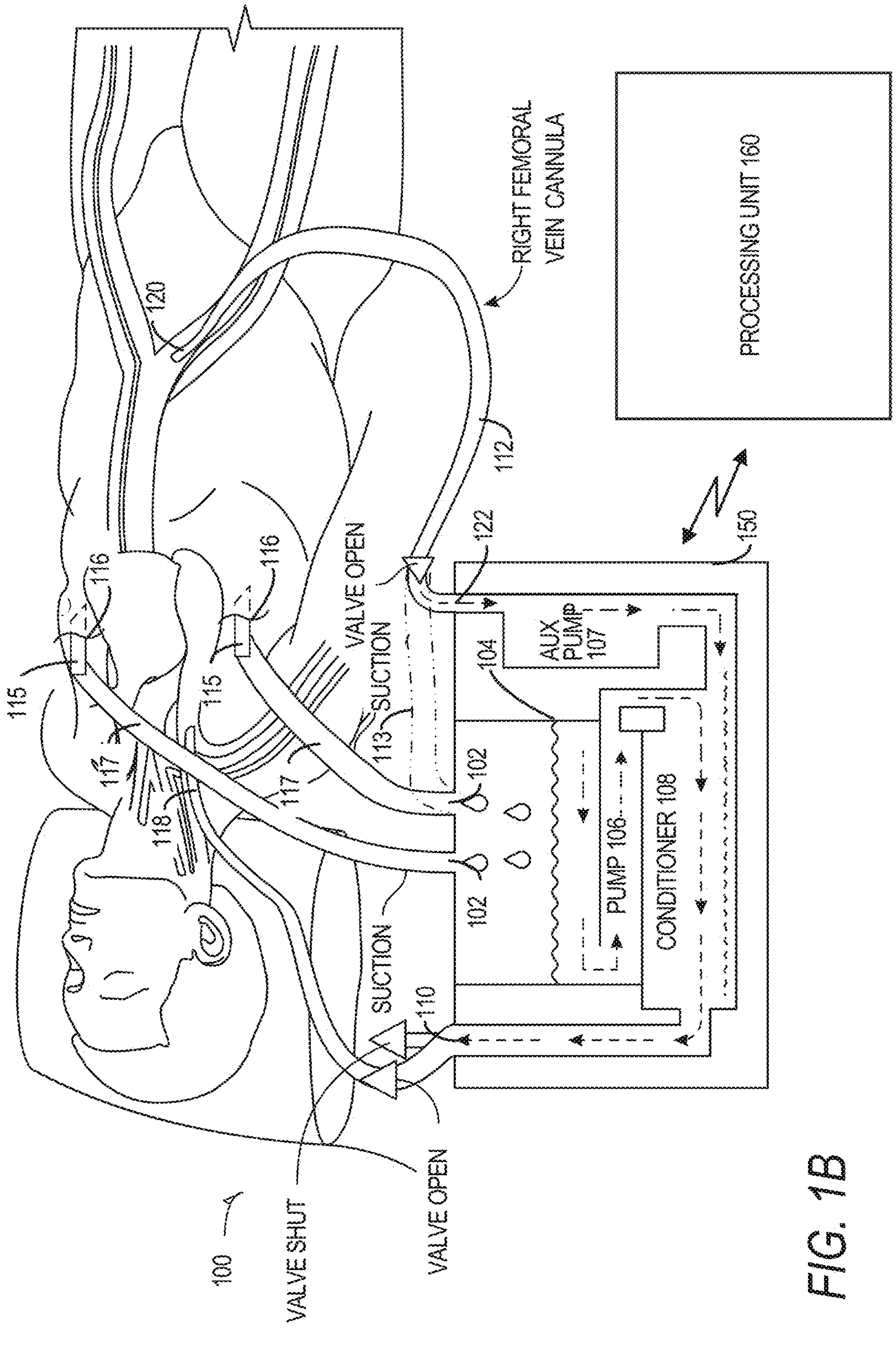
FIG. 1B depicts an example of a system for performing extracorporeal blood treatment of blood recovered from a subject.
Figure 1C:
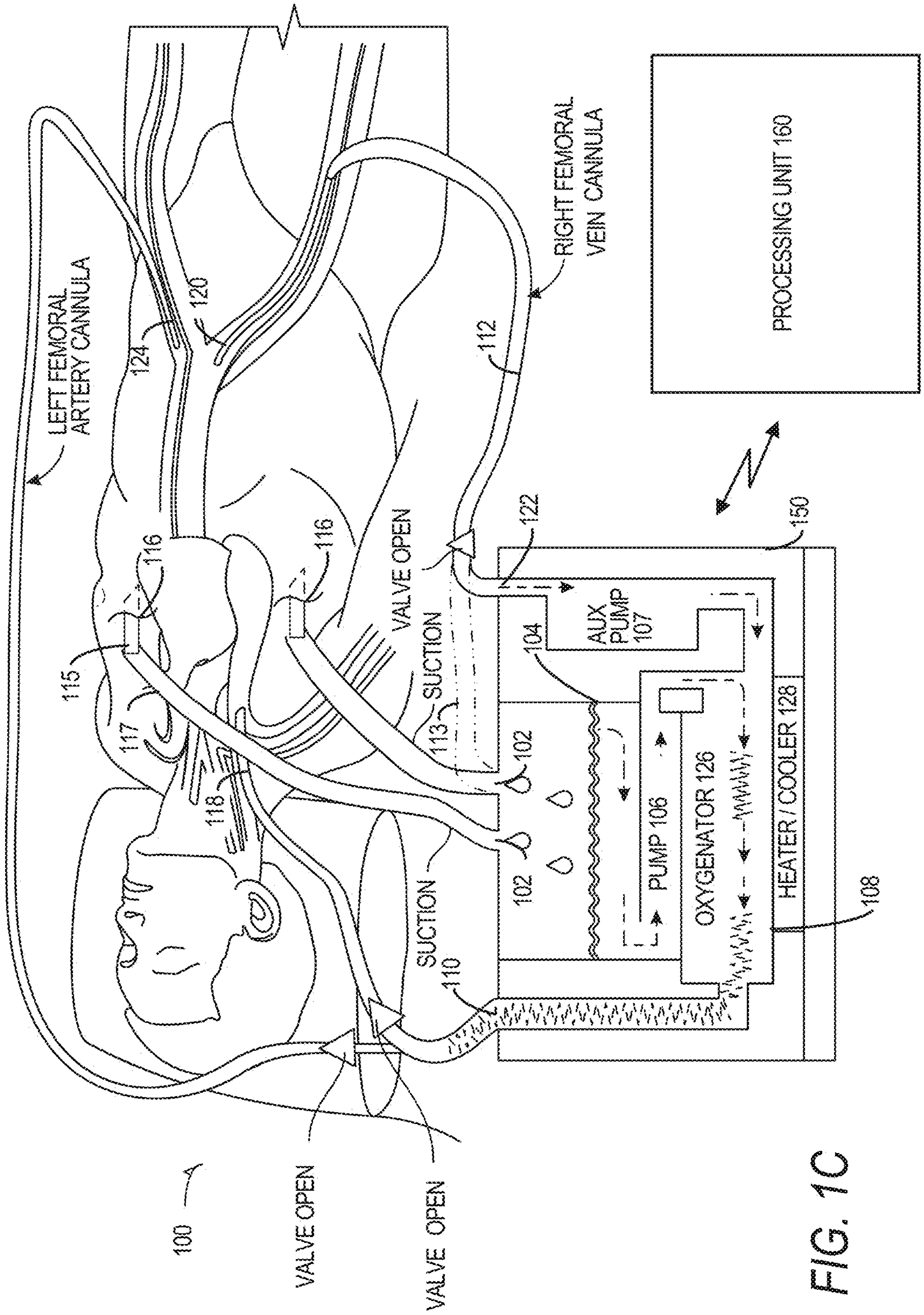
FIG. 1C depicts an example of a system for performing extracorporeal blood treatment of blood recovered from a subject.

FIG. 1A, FIG. 1B, and FIG. 1C each depicts an example of a system for performing extracorporeal blood treatment of blood recovered from a subject. The system 100 can include a blood treatment device 150 including at least one first fluid inlet 102, a reservoir 104, a pump 106, a conditioner 108, and a first fluid outlet 110. The system can be configured to perform according to a plurality of different operating modes, and an individual mode can be selected based at least in part on a medical condition of the subject. For example, the system 100 can include a processing unit 160 included in, or otherwise communicatively coupled with, the blood treatment device 150. The processing unit 160 can include processing circuitry for monitoring at least one parameter of the blood recovered from the subject and to establish or adjust an operating parameter of the blood treatment device 150 based on the monitored blood. Ultimately, the plurality of different operating modes can be serially performed such as to progressively escalate treatment of the subject. Selection of an individual operating mode can at least in part be based on an indication of blood volume recovered, arterial blood gas (ABG), or an indication of blood lactate of the subject.

As depicted in FIG. 1A, the system 100 can perform according to an initial operating mode. The initial operating mode, also referred to herein as the "assist" mode, can be considered a standard or default operating mode of the system 100 and can be performed as a starting point for blood conditioning. For example, the initial operating mode can be initiated before receiving any indications of blood parameters. Blood can be received from a first blood transfer location 116 of the subject. Herein, "blood" can refer to mammalian whole blood, mammalian blood components such as red blood cells, platelets, and blood plasma, or another formulation of components which includes, at least in part, mammalian blood components. In an example, the first blood transfer location 116 can be a wound, an open surgical location, a bleeding site, or other type of fluid loss or hemorrhage location. In an example, the first blood transfer location 116 can correspond with an intrathoracic or intra-abdominal space of the subject, such as in the pleural cavity, the peritoneum, the retroperitoneal space, the thoracic or abdominal cavities. The first blood transfer location 116 can also correspond with a surgical location or an injury site in the extremities, such as a limb of the subject.

The system 100 can facilitate blood recovery from an intrathoracic area where the subject has sustained a wound or other pericardial or lung injury where access from exterior regions of the subject's body is undesired or unfeasible. For example, the system 100 can include or use a trocar 115 configured for tissue perforation and fluid or blood management. In an example, the trocar 115 can be sized and shaped to be inserted into the subject at the first blood transfer location 116. For example, the trocar 115 can include a diaphragm portion and a removable cannula. The diaphragm portion can be seated, via insertion of the cannula, at the first blood transfer location 116. The diaphragm portion can be expandable via inflation, vacuum, spring bias, or a similar mechanism to substantially secure and seal the diaphragm portion within the subject at the first location 116. In an example, the cannula can be removed following the seating of the diaphragm portion, and the diaphragm portion can establish a port into the intrathoracic or the intra-abdominal space of the subject. The system 100 can include or use a tube or conduit 117 sized and shaped to be inserted into the port for drawing blood from the subject and toward the blood treatment device 150.

The at least one first fluid inlet 102 of the blood treatment device 150 can be fluidly coupled to the tube or conduit 117. In an example, the system 100 can include or use a source of suction, e.g., a vacuum pump, to facilitate drawing of the blood from the first blood transfer location 116 and toward the reservoir 104. Alternatively or additionally, blood can be drawn from the first blood transfer location 116 passively, e.g., via gravity. For example, the blood treatment device 150 can be positioned such that the first blood transfer location 116 is at or near about or above a level of the reservoir 104, and such that gravitational forces can assist in directing the blood at least toward the first fluid inlet 102. As depicted, the first blood transfer location 116 can be accessed by a plurality of lines, such as via a plurality of trocars 115 or cannulas, for receiving blood into the reservoir 104. Multiple lines for drawing blood from the first blood transfer location 116 can be helpful, e.g., when an internal bleed spans a relatively wide area.

The reservoir 104 can collect the drawn blood, and an inline pump 106 fluidly coupled with the reservoir can move the blood toward the conditioner 108. In an example, the conditioner 108 can facilitate removal of carbon dioxide ($CO_2$) from the blood before redistribution of the conditioned blood out of the first fluid outlet 110 and back to the subject. Alternatively or additionally, the conditioner 108 can regulate a temperature of the blood before similar redistribution. In the initial operating mode, the conditioned blood can be administered to the subject intravenously at a first return location 118 of the subject, e.g., into an internal jugular vein of the subject. Components of the blood treatment device 150, such as the reservoir 104, the inline pump 106, and the conditioner 108, are discussed in greater detail below with reference to each substantially similar component depicted in FIG. 2*a* and FIG. 2B.

In an example, the system 100 can include or use a reservoir bypass circuit 112. The reservoir bypass circuit 112 can be fluidly coupled to a primary fluid circuit of the blood treatment device 150. The reservoir bypass circuit 112 can be arranged such as to provide recovered blood from the subject, via a second fluid inlet 122, drawn from the subject via an auxiliary pump 107 toward the conditioner 108 and without entering the reservoir 104. For example, the reservoir bypass circuit can include or use the auxiliary pump 107 located in the reservoir bypass circuit 112 to help move recovered blood from the second fluid inlet 122 toward the conditioner 108. Alternatively or additionally, the system 100 can use a single pump, the inline pump 106, both for the primary fluid circuit and the reservoir bypass circuit 112. As depicted in FIG. 1A, the initial operating mode can involve the reservoir bypass circuit 112 being disengaged, disconnected, or otherwise not used, such that the inline pump 106 moves the entirety of the blood recovered from the subject through the reservoir 104. As depicted in FIG. 1A, FIG. 1B, and FIG. 1C, various circuits and fluid lines can be selectively engaged or disengaged via one or more actuators arranged to control respective valves of the circuit. For example, as shown in FIG. 1A and FIG. 1B, the processing unit 160 can control the one or more actuators such as to selectively engage or disengage the reservoir bypass circuit 112 and to initiate a particular operating mode. Alternatively, the various circuits and fluid lines can be manually clamped or disconnected from the primary fluid circuit at one or more locations, e.g., by a user, to selectively engage or disengage rather than be controlled by valves and actuators. In the initial operating mode, the second fluid inlet 122 is not used for blood recovery, no auxiliary pump 107 (if included) is active, and the entirety of the conditioned blood is received from the subject at the first blood transfer location 116, passed through the reservoir and exclusively through the inline pump 106 before being conditioned and distributed back to the subject exclusively at the first return location 118. In an example, the system 100 can condition blood at a flow rate within a range of about 1 liter per minute (L/min) and about 5 L/min while in accordance with the initial operating mode.

The blood treatment device 150 can be communicatively coupled with the processing unit 160. For example, the processing unit 160 can be located onboard the blood treatment device 150, or instead can be communicatively linked such as via wired or wireless connection. The processing unit 160 can include or use software for implementing one or more algorithms to monitor blood received from the subject and to establish or adjust at least one operating parameter of the conditioner 108 based on the monitored blood. For example, the at least one operating parameter can include a flow rate of the pump 106, a temperature regulation parameter of the conditioner 108, an oxygenation parameter of the conditioner 108, or an alert for an operator to move from the initial operating mode of the system 100 toward a different operating mode. In an example, the processing unit can include or use a machine learning model to determine an optimal set of parameter settings for the blood treatment device 150, conditioner 108, or other components (e.g., a sensor, valve, or pump). The machine learning method can continuously take measurement of data from the components over time, or when the device is turned on or re-initialized, in order to continuously iteratively improve the estimate to an optimal set of parameter settings. For example, the optimal set of parameter settings can include one or more desired blood flow rate settings or one or more granularity levels for the blood volume lost, temperature, oxygenation, or PH levels of the blood from the subject. Also, the processing unit 160 can predictively model blood or therapy requirements of the subject. For example, the processing unit 160 can include or use stored data to extrapolate, interpolate, or otherwise estimate likely future diagnosis or blood requirement of the subject. Such an estimation can be iteratively revised with subsequently received data.

FIG. 1B depicts an optional, intermediate operating mode of the system 100. The intermediate operating mode, also referred to herein as the "acidosis mode", is substantially similar to the initial operating mode described above with reference to FIG. 1A. In an example, during performing the initial operating mode, the processing unit 160 can determine that a lactate concentration of the subject is worsening beyond a threshold parameter, such as a lactate concentration measured or predicted within a range of about 3 millimoles per liter (mmol/L) and about 5 mmol/L. Such a worsening trend can indicate that a subject is moving toward (or is in) a dangerous situation such as approaching lactic acidosis or an oxygen demand for blood that the subject will be unable to meet under the present operating parameters. Therefore, the processing unit 160 can generate or output a signal to the pump 106 or conditioner 108 to shift toward the intermediate operating mode. Here, the intermediate operating mode can involve temporarily increasing or intensifying the amount of therapy delivered via the system 100 in response to the determination that the lactate concentration is worsening beyond the threshold parameter. For example, the processing unit 160 can output a signal to the pump 106 or conditioner 108 to adjust a flow rate, temperature, oxygenation, or sweep gas parameter such as to increase a therapeutic effect of the system 100 on the subject. For example, the intermediate operating mode can involve the system 100 adjusting one or more operating parameters such as to condition the blood at a flow rate within a range of about 0.5 liters per minute (L/min) and about 7 L/min.

In an example, to help counteract a worsening trend in lactate concentration of the subject, performing the intermediate operating mode can involve drawing intravenous blood from the subject, such as via an intravenous cannula inserted at a second blood transfer location 120. For example, blood can be received from a femoral vein of the subject, e.g., to increase a fluid throughput and conditioning capacity of the system 100. As depicted in FIG. 1B, the intravenous blood drawn from the second blood transfer location 120 can be received at the second fluid inlet 122 and can enter the blood treatment device 150 via the reservoir bypass circuit 112. Alternatively or additionally, the intermediate operating mode can involve drawing intravenous blood from the subject at the second blood transfer location 120 and receiving the drawn intravenous blood at the at least one first fluid inlet 102 (according to the alternative depiction via phantom lines at 113). Here, the intravenous blood drawn from the second blood transfer location 120 can pass through the inline 106 without a need for the auxiliary pump 107 and without entering the reservoir bypass circuit 112. Both a blood volume received from the first blood transfer location 116 and a blood volume received from the second blood transfer location 116 can be conditioned via the conditioner 108 and administered back to the subject via the cannula into an internal jugular vein.

FIG. 1C depicts a controlled preservation mode of the system 100. Generally, the controlled preservation mode can be initiated to temporarily slow biological function of the subject such as to help preserve organ tissue. In an example, a controlled preservation mode of the system 100 can condition the subject's blood such as to induce a state of deep hypothermic arrest. Without being bound by theory, inducing a state of deep hypothermic arrest in the subject, toward a state of suspended animation, can lower a cardiac demand and can slow an increase of intercranial pressure for a subject experiencing TBI (Traumatic Brain Injury) and lactic acidosis.

In an example, during the performing of at least one of the initial operating mode or the intermediate mode, the processing unit 160 can determine, based on an indication that at least one of lactate concentration or ABG levels are worsening beyond a threshold parameter such that the subject is at or near a state of uncompensated shock or lactic acidosis. The transitioning to the controlled preservation mode can be based at least in part on a determination of a blood volume loss at a value between about 500 mL and about 1600 mL or at a value between about 750 mL and about 1500 mL. In an example, the transitioning to the controlled preservation mode can be based at least in part on a determination of a lactate concentration at or approaching a threshold value between about 1 millimole per deciliter (mmol/dL) and about 3 mmol/dL, such as a lactate concentration at or approaching less than about 2 mmol/dL. The transitioning to the controlled preservation mode can be based at least in part on a determination of ABG PH level at or less than around 7.2. Similarly, the transitioning to the controlled preservation mode can be based on a determination of blood pH at or approaching a threshold value between about 7.2 and 7.35, such as between about 7.25 and 7.3. The transitioning to the controlled preservation mode can be based at least in part on a determination of the subject's partial pressure of arterial oxygen ($PaO_2$) at or approaching a threshold value less than about 60 millimeters of mercury (mmHg). Further, the transitioning to the controlled preservation mode can be based at least in part on a determination of the subject's partial pressure of $CO_2$ ($PCO_2$) at or approaching a threshold value greater than about 45 mmHg.

Before implementation of the controlled preservation mode, the system 100 can administer an alert or a prompt for a user, such as a technician or medical professional, to initiate a transition toward the controlled preservation mode by preparing 1) the second blood transfer location 120 at a femoral vein of the subject (if not yet used for intravenous drawing of blood) and 2) a second return location 124 at a femoral artery of the subject for intra-arterial return of conditioned blood. For example, the alert or prompt can instruct the user to cannulate the second blood transfer location 120 and the second return location 124 before authorizing implementation of the controlled preservation mode. As depicted in FIG. 1C, the blood treatment device 150 can draw blood from the second blood transfer location 120 via the reservoir bypass circuit, through the second fluid inlet 122. Here, the drawn blood can be introduced to the conditioner 108 via the auxiliary pump 107. Alternatively or additionally, the blood treatment device 150 can receive blood from the second blood transfer location 120 through the at least one first fluid inlet 102, into the reservoir, and via the inline pump 106 (according to the alternative depiction via phantom lines at 113). Thus, here a single pump (the inline pump 106) can move blood from the first blood transfer location 116 and the second blood transfer location 120 into the reservoir and toward the conditioner during operation of the controlled preservation mode.

In an example, the processing unit 160 can receive confirmation that the second blood transfer location 120 and the second return location 124 have been prepared to initiate the controlled preservation mode. Upon initiation of the controlled preservation mode, the processing unit can adjust operating parameters such as to lower a temperature of the conditioned blood toward a target first temperature within a range of about 30° C. and about 40° C. (e.g., toward a target first temperature of about 33° C.) via a heater/cooler 128 included in the blood conditioner 108. Returning blood to the subject at or near the target first temperature can lower the subject's myocardial oxygen demand and provide the subject's body at least temporary relief in an attempt to pull the subject out of uncompensated shock or lactic acidosis. The processing unit 160 can continue to monitor ABG levels and blood lactate concentration, following initiation of the controlled preservation mode, such as to determine whether a subject's state is improving or deteriorating. If the subject's state continues to deteriorate, the processing unit 160 can further adjust operating parameters such as to lower a temperature of the conditioned blood toward a target second temperature with a range of about 10° C. and about 25° C. (e.g., toward a target second temperature of about 18° C.) via the heater/cooler 128 and such that the conditioned blood is supplied to the subject at a relatively low target flow rate within a range of about 1 L/min and about 3 L/min, or within a range of about 1.5 L/min and about 2 L/min. The processing unit 160 can also facilitate administration of one or more pharmaceutical agents, selected to extend a time the subject can be suspended via deep hypothermic arrest and to limit ischemia-reperfusion injury (IRI) or reoxygenation injury. For example, the processing unit 160 can facilitate the administration of at least one of lidocaine, magnesium, nicardipine, milrinone, mannitol, calcium, magnesium, a pH-stat, or an alpha-stat. During suspension of the subject in deep hypothermic arrest, the processing unit 160 can continue to monitor a subject's condition. For example, the processing unit 160 can monitor at least one of body temperature, activated clotting time (ACT), ABG levels, or blood lactate concentration.

Operating the system 100 in the controlled preservation mode can afford a surgeon or other medical professional time to perform damage control physiological resuscitation (DCPR). For example, surgery can be performed during maintenance of temporary circulatory arrest via the processing unit 160 and via control of the conditioned blood supplied to the subject at the target second temperature and at the target flow rate. Once adequate surgical control of bleeding is achieved, a user can employ the blood treatment device 150 to slowly bring the subject back out of the induced state of deep hypothermic arrest and return the subject toward normal body temperature and blood flow rate. For example, the processing unit 160 can facilitate rewarming of the blood returned to the subject at the first return location 118 and the second return location 124. For example, the processing unit can monitor at least one of a temperature of the blood being intravenously returned to the first return location 118 or the temperature of the conditioned blood exiting an oxygenator 126 of the blood conditioner. In an example, the processing unit can calculate a target blood rewarming speed, such as to minimize air embolization. For example, the target blood rewarming speed can be within a range of about 0.1 degrees Celsius per minute (° C./min) and about 0.7° C./min, such as within a range of about 0.25° C./min and about 0.5° C./min.

Figure 2A:
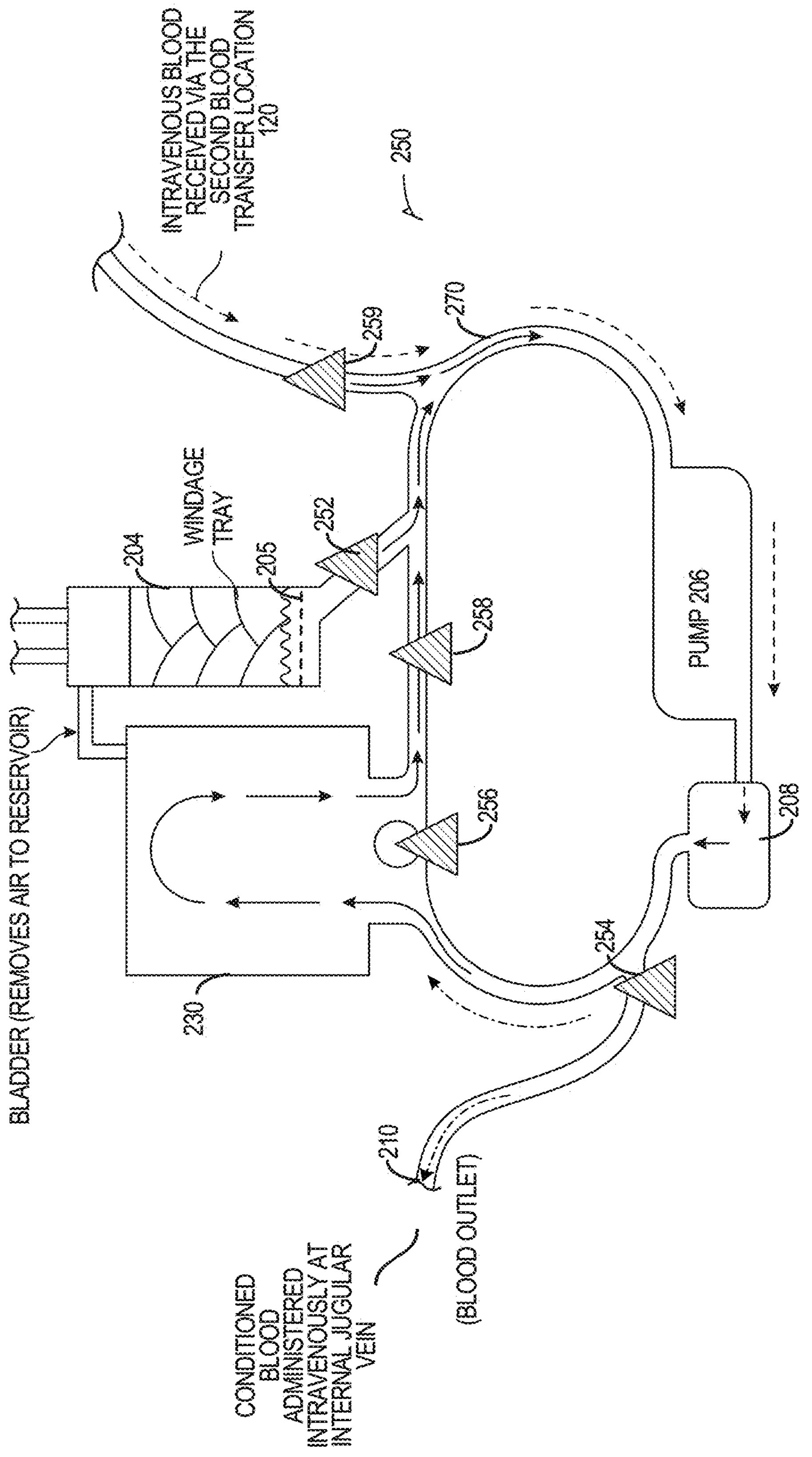
FIG. 2A depicts an example of a blood treatment device.
Figure 2B:
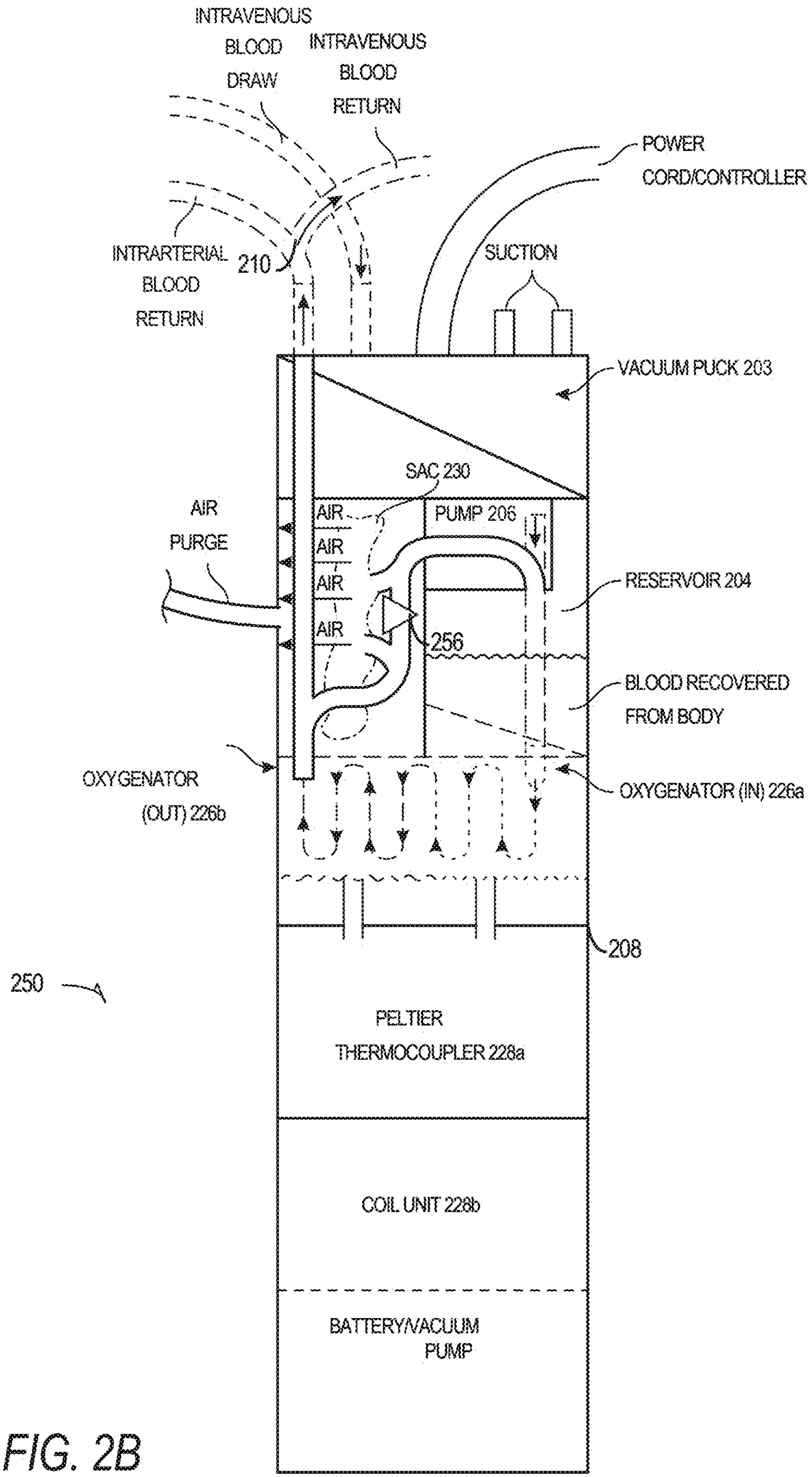
FIG. 2B depicts an example of a blood treatment device arranged within an enclosure.
Figure 2C:
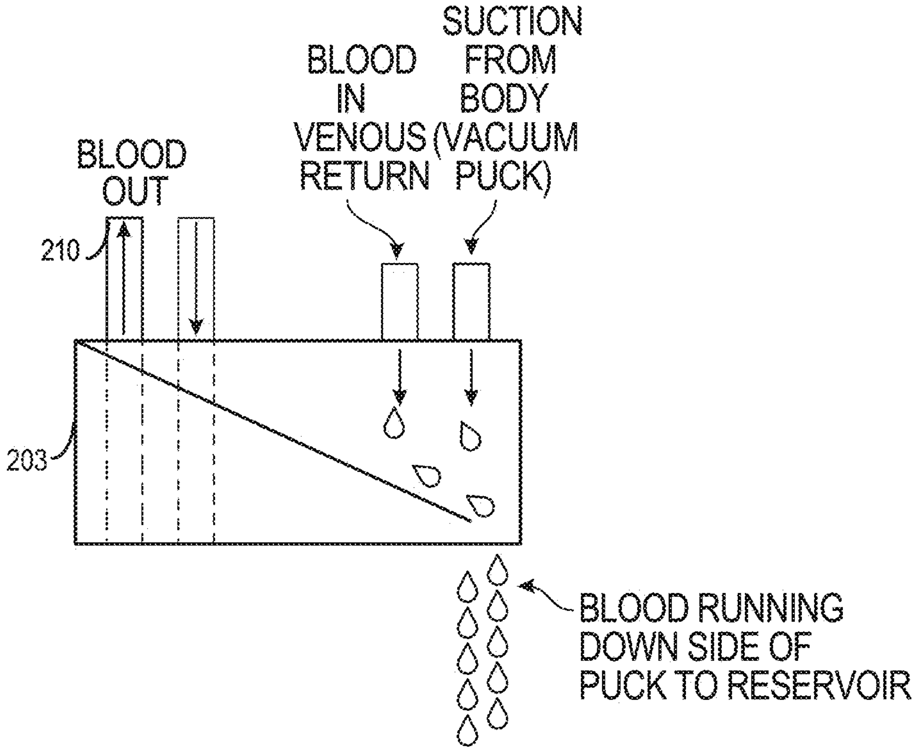
FIG. 2C depicts an example of a vacuum puck of a blood treatment device.

FIG. 2A and FIG. 2B each depict an example of a blood treatment device 250. The blood treatment device 250 is substantially similar to the blood treatment device 150 of FIG. 1A, FIG. 1B, and FIG. 1C. The components, structures, configurations, functions, etc. of the blood treatment device 250 can therefore be the same as or substantially similar to that described in detail above with reference to the blood treatment device 150. In an example and as depicted in FIG. 2A, the intravenous blood received via the second blood transfer location 120 (e.g., the femoral vein of the subject) can be incorporated into the primary fluid circuit 270 upstream of the pump 206. The blood treatment device 250 can further include an enclosed sac, bladder, vesica, or bag 230 fluidly coupled with the blood conditioner 208 and arranged to receive conditioned, recovered blood therefrom. The enclosed sac 230 can facilitate air purging from the primary fluid circuit 270 concurrent with blood treatment via the conditioner 208 and without stopping fluid flow or employing an air lock. For example, the enclosed sac can include a permeable or semipermeable membrane configured to contain fluid such as blood products while allowing diffusion of air and other gases through the membrane. In an example, the semipermeable membrane can include at least one of a microporous, nanoporous, chemical semi resistant, or chemical resistant, or anti-fouling polymer based material or other material or combination of materials having desired gas exchange or diffusion qualities while not permitting blood to permeate from the sac. The gas diffused from the sac 230 can be transported to an air evacuation port of the sac 230 and into the gas headspace of the reservoir 204. In another example, the gas diffused from the sac 230 can be released to the ambient environment. The enclosed sac 230 can also be fluidly coupled to the reservoir 204, such as establishing an open loop hydraulic circuit with the recovered blood. Herein, an "open loop" circuit refers to configurations in which fluid is recirculated and selectively supplied to different locations while not fully recirculating the fluid to its original source. For example, the sac 230 can be fluidly coupled directly to an outlet of the reservoir 204 and fluidly coupled directly to an outlet of the conditioner 208. Also, herein the term "fluidly coupled" permits intervening, openable two-way valves such as valves 252, 254, 256, 258, and 259 depicted in FIG. 2. In an example, the primary fluid circuit 280 can include a valve 254 disposed between the sac 230 and conditioner 208, and the valve 254 can be operable to divert recovered blood exiting the sac 230 toward a blood outlet for redistribution back to the subject (e.g., via the internal jugular vein of the subject). For example, the valve 254 can be a diverter valve, a Y-valve, or a single two-way valve disposed on one end of a three-way or Y-shaped junction disposed between the sac 230 and the conditioner 208. The fluid circuit 270 can include a reservoir valve 252 and a cannulated blood line valve 259 which can be respectively engaged to allow a first portion of recovered blood from the reservoir and a second portion of recovered blood from the second blood transfer location 120 to be introduced into the primary circuit 270. In an example, the sac 230 can include a plurality of fluid connections with the primary circuit 270 and at least one bridge valve 256 disposed between the plurality of fluid connections. The bridge valve 256 can be opened to help equalize any pressure buildup within the sac 230 across the fluid circuit 270. For example, the bridge valve 256 can be temporarily opened when the reservoir valve 252 is closed to relieve excess volume accumulated in the sac 230. Thus, the reservoir valve 252 can facilitate protection of the red blood cells and Hb of the blood volume in the sac 230, such as preventing or limiting collapsed Hb from excess pressure. The fluid circuit 270 can also include a drainage valve 258. The drainage valve 258 can generally remain in an open position during operation of the device 250. However, when the reservoir valve 252 is opened and blood is being received by the fluid circuit 270 from the reservoir 204, the drainage valve 258 can be closed to help case drainage from the reservoir 204. Also, when the drainage valve 258 is open, recovered blood from the sac 230 can reenter the circuit directly downstream of the reservoir 204 and be again circulated via the pump 206. Each of the valves 252, 254, 256, 258, and 259 can be independently engaged with respect to one another and can each be operated via a mechanical actuator, an electromechanical actuator, a pneumatic actuator, a solenoid actuator, a motorized actuator, a hydraulic actuator, a magnetic actuator, a computer actuator or microcontroller, a bimetallic strip, or a combination thereof.

FIG. 2B depicts the blood treatment device 250 arranged within an enclosure. Such a compact arrangement can facilitate blood treatment methods described herein in non-hospital settings or in resource-poor environments. In an example, the blood treatment device can include or use a vacuum puck 203 arranged adjacent to the reservoir 204 and connected to a fluid headspace of the reservoir 204. As shown in the detail view in FIG. 2C, blood entering the vacuum puck 203 via the first blood transfer location 116 or the second blood transfer location 120 (depicted in FIG. 1B) can run down a side of the vacuum puck 203 toward the reservoir. In an example, the vacuum puck 203 can include a ramp or tilt such as to force blood down the side of the reservoir. In an example, a source of suction, such as an onboard vacuum unit, can facilitate suction of the blood into the reservoir 204 at a flow rate within a range of about 1 L/min and about 10 L/min, or within a range of about 2 L/min and about 6 L/m, e.g., at or near a flow rate of about 4 L/min. In an example, the source of suction can be disabled or impeded during an emptying of the reservoir 204 into the fluid circuit 270, such as when the valve 252 is opened (as depicted in FIG. 2A). In an example, the valve 252 can include an actuator or an additional intermittent pump that pulls blood from the reservoir.

The reservoir 204 can include or use a first filter for separating out larger particulates or unwanted materials, e.g., dirt, or metallic fragments from the blood or other fluid being transported into the reservoir. The first filter can also be arranged to prevent clots or larger proteins, such as fibrin, from progressing further along a fluid circuit of the primary circuit 270. The reservoir can also include a second filter for filtering ambient air that is drawn into the reservoir, such as to help maintain a sterile environment. The reservoir can also include or use windage tray, bubble-trap, or air separation chamber arranged to block or divert gases (e.g., bubbles or foam) away from the reservoir and to prevent gases from progressing further along the primary circuit 270. For example, the windage tray can provide a physical barrier between gases and blood or other fluid, and the windage tray can have openings arranged to allow lower density gases or air to rise and be vented or removed to an external atmosphere or be collected and processed. In situations where the reservoir becomes canted or inverted during the drawing of the blood from the first blood transfer location 116 into the reservoir, the windage tray can establish or maintain a desired or predetermined surface level of the fluid, e.g., the blood or other body fluid being processed or treated. For example, the windage tray can facilitate that the drawn blood or other body fluid is held at or above a predetermined surface level (e.g., corresponding with the dotted boundary 205 as shown in FIG. 2A) in the reservoir 204. This can help prevent unwanted bubbles or gases from entering the suction source or suction line, thereby preventing unwanted pressure surges and sudden flow increases. In an example, the windage tray can include or use one or more physical separation elements, such as baffles, vanes, grates, or textured surfaces.

The reservoir 204 can be sterile and fluidly sealed relative to an external ambient environment. The reservoir 204 can maintain a negative internal pressure relative to the external ambient environment, and the negative internal pressure can be provided at least in part by the source of suction. In an example, the reservoir 204 can include a reservoir pressure relief valve for the source of suction, and the pressure relief valve can be selectively engageable in response to detection of a clogging or obstruction at the trocar or chest tube. The reservoir pressure relief valve can help prevent damage to the reservoir 204 or to the tissue at the first blood transfer location 116 (as depicted in FIG. 1A). The reservoir 204 can include one or more filtration or air separation elements arranged therein to limit air bubbles, contaminates, or other unwanted components from further traveling in the fluid circuit of the blood treatment device 250. In an example, the reservoir 204 can be filled with blood toward a maximal internal volume, the maximum internal volume being within a range of about 500 cubic centimeters (cc) and about 2000 cc. In an example, the reservoir 204 can include or contain an anticoagulant such as heparin, bivalirudin, argatroban, enoxaparin sodium, a tissue-type plasminogen activator (tPA) or another anticoagulant or antiplatelet. Here, the anticoagulant can prevent subsequent clotting or clot formation within the blood treatment device 250. The anticoagulant, for example, can be added to the reservoir 204 prior to the blood being conveyed into the reservoir, mixed with the blood, or otherwise distributed with the blood within the blood treatment device 250.

The pump 206 can be arranged inline and spaced apart from (e.g., located upstream) the conditioner 208. The pump 206 can include a centrifugal blood pump (CBP) such as a magnetically levitated (maglev) pump, an impeller pump, a vaneless pump, a bearingless pump, or a combination thereof. The pump 206 can be configured to facilitate continuous pumping and delivery of blood from the reservoir toward and through the oxygenator. Herein, "continuous flow" can refer to blood flow over a significant period (e.g., greater than about 5 seconds) wherein the blood flow curve is substantially free of discontinuities (e.g., less than about 10% fluctuation in flow rate). When the fluid circuit of the blood treatment device 250 is subject to greater than a threshold flow resistance (e.g., greater than 200 mmHg/L/hr) downstream of the pump 206 (e.g., caused by a kink or obstruction in a fluid line), a CBP can respond by decreasing its speed or decreasing the rate at which it propels the blood until the flow resistance decreases. As such, a CBP can be advantageous to certain other blood pumps, such as in reducing damage to the blood by avoiding g-forces or transmembrane pressure gradients caused by high accelerations or decelerations. A CBP can also be advantageous in a fluid circuit in that it can withstand kinks or obstructions to the fluid line without bursting a fluid line or otherwise breaking a fluid seal of the fluid circuit. Alternatively or additionally, the pump 206 can include a pulsatile pump such as a roller pump, a diaphragm pump, or a peristaltic pump configured to facilitate pulsatile flow of the blood. The pulsatile pump can be configured to emulate a physiologic pulsatile flow of blood, e.g., a flow having a pulse waveform in a range of physiological pulse waveforms. Where the pump includes a pulsatile pump such as a roller pump, the primary circuit 270 can include one or more pressure sensors and the roller pump can be controlled (e.g., via a processing unit) to slow or stop a pumping operation where the system detects greater than a threshold line pressure caused by a kink or and obstruction. Moreover, if desired, when the system detects a decrease in blood flow caused by kinking or obstruction of a downstream fluid line, the system can either operate the pulse pump to increase flow from a zero (or minimum pulse volume) or have the system transition to a continuous-flow mode of operation.

As depicted in FIG. 2B, the blood conditioner 208 can include an oxygenator 226, a temperature regulator 228, or both. For example, an oxygenator 226 of the blood conditioner can include a silicon oxygen membrane or polymethylpentene (PMP) membrane for removing carbon dioxide ($CO_2$) from the recovered blood. Once $CO_2$ is removed, the recovered blood can cleave to hemoglobin (Hb) supplied in the oxygenator at a sweep gas rate within a range of about 2 L/min to about 6 L/min or about 4 L/min, and at a fraction of inspired oxygen ($FiO_2$) between about 10% and about 50% or an $FiO_2$ between about 21% and about 100%. In an example, the recovered blood passed through the oxygenator 226 of the blood conditioner can be hyper oxygenated, such as having a $PaO_2$ greater than about 100 millimeters of mercury (mmHg) or greater than about 200 mmHg. In an example, the blood conditioner 208 can use ambient air, such as ambient air exhausted from a vacuum pump or other source of suction, to help oxygenate the recovered blood. For example, the blood conditioner 208 can regulate a flow of ambient air between about 6 L/min and about 10 L/min, or at about 8 L/min. Also, supplemental $O_2$ can be supplied, e.g., via an external or onboard tank, in addition to the ambient air. For example, the supplemental $O_2$ can be supplied to help increase a net flow of air or sweep gas rate. Here, the supplemental $O_2$ can be supplied at a rate within a range of about 1 L/min and about 2 L/min. As such, the blood conditioner 208 can provide a net sweep gas rate between about 6 L/min and about 10 L/min while relying on supplemental $O_2$, provided via the external or onboard tank, being supplied a flow rate of less than 2 L/min.

The blood conditioner 208 can also include one or more heater/cooler units, such as a Peltier thermocoupler **228*a* and a coil unit 228*b*. In an example, the Peltier thermocoupler 228 can facilitate preheating of the recovered blood before it enters the oxygenator 226, such as to improve the oxygenation of the blood. This is because increased temperature has an inverse relationship to reaction time (e.g., removal of $CO_2$ and cleaving to hemoglobin (Hb)) and increases the rate of reaction, such that as the temperature increases, the number of molecules existing at higher energy levels increases. Also, the recovery blood may need to be cooled, involving the Peltier thermocoupler 228*a* and a coil unit 228*b* to heat exchange the recovered blood from room temperature to a desired temperature range. For example, with reference to the controlled preservation mode of FIG. IC, the coil unit 228*b* can be used by the blood treatment device 250 to induce a state of deep hypothermic arrest or ventricular fibrillation in the subject. This can range from, for example, a targeted temperature within a range of about 10° C. and about 30° C. The Peltier thermocoupler 228*a* and the coil unit 228*b* can work in conjunction with each other or alone. In an example, the temperature regulator 228 can be physically separate from the oxygenator 226**, with the recovered blood passed back and forth, or the temperature regulator and oxygenator can be physically integrated.

Figure 3:
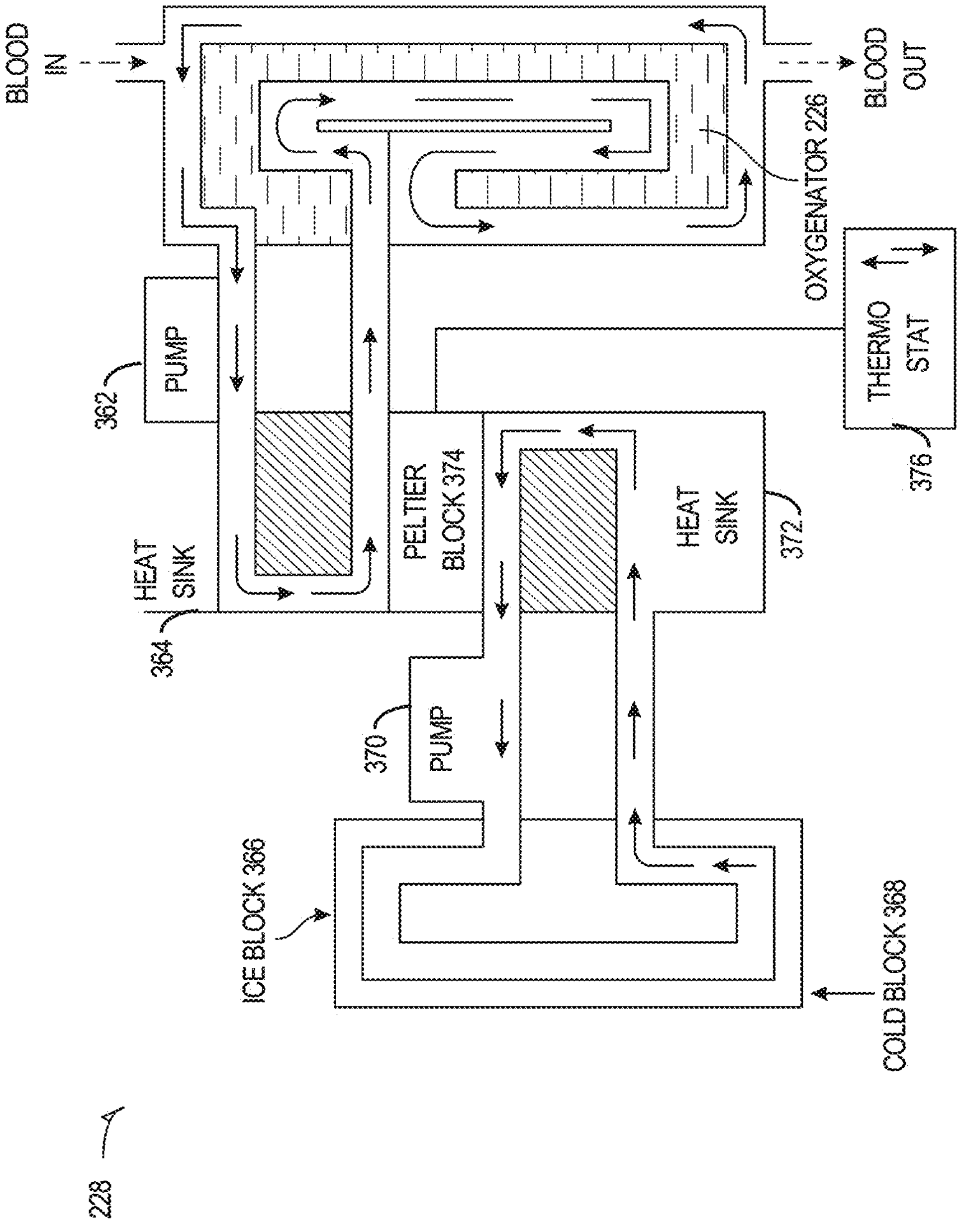
FIG. 3 depicts an example of an integration of the temperature regulator with the oxygenator in an example of a blood conditioner.

FIG. 3 shows an example of an integration of the temperature regulator 228 with the oxygenator 226 in a blood conditioner 208. For example, the blood conditioner 208 can include or use the oxygenator 226, an oxygenator pump 362, an oxygenator heat sink 364, an ice block 366, a cold block 368, a temperature regulator pump 370, a temperature regulator heat sink 372, a Peltier block 374 disposed between an oxygenator circuit and a temperature regulator circuit, and a thermostat 376. The oxygenator pump 362 can draw the recovered blood, e.g., from the reservoir 204 (as depicted in FIG. 2B). As the recovered blood passes through the oxygenator 226, $CO_2$ gas can be extracted from the recovered blood by diffusion across the oxygenator membrane. The rate of removal of $CO_2$ can be enhanced by concentrating a $CO_2$ sweep gas close to the surface of the membrane.

The Peltier block 374 can provide both heating and cooling output through separate interfaces via manipulation of electrical potential difference. Further, the Peltier block 374 can be compact, reliable, and efficient in thermoelectric cooling and heating applications involving heat exchange. Thus, the Peltier block 374 can be integrated in the blood conditioner 208 to operate in both cooling and heating modes, thereby providing an integrated cooling warming platform that can be used in a blood treatment device. In an example, the Peltier block 374 can function as a stand-alone heating element or cooling element utilizing temperature gradient with power provided to the Peltier block 374. Activation can be bi-directional to both heat and cool the functional blocks with switching capability. This can be accomplished via an electrical power controller system, which can direct the electrical current to the Peltier block 374 resulting in a change of direction of heat transfer and thus exchange. Such an arrangement can yield an efficient, rapid time response for blood heating and cooling operations to the desired temperature (e.g., within a range of about 10° C. and about 30° C.).

Figure 4A:
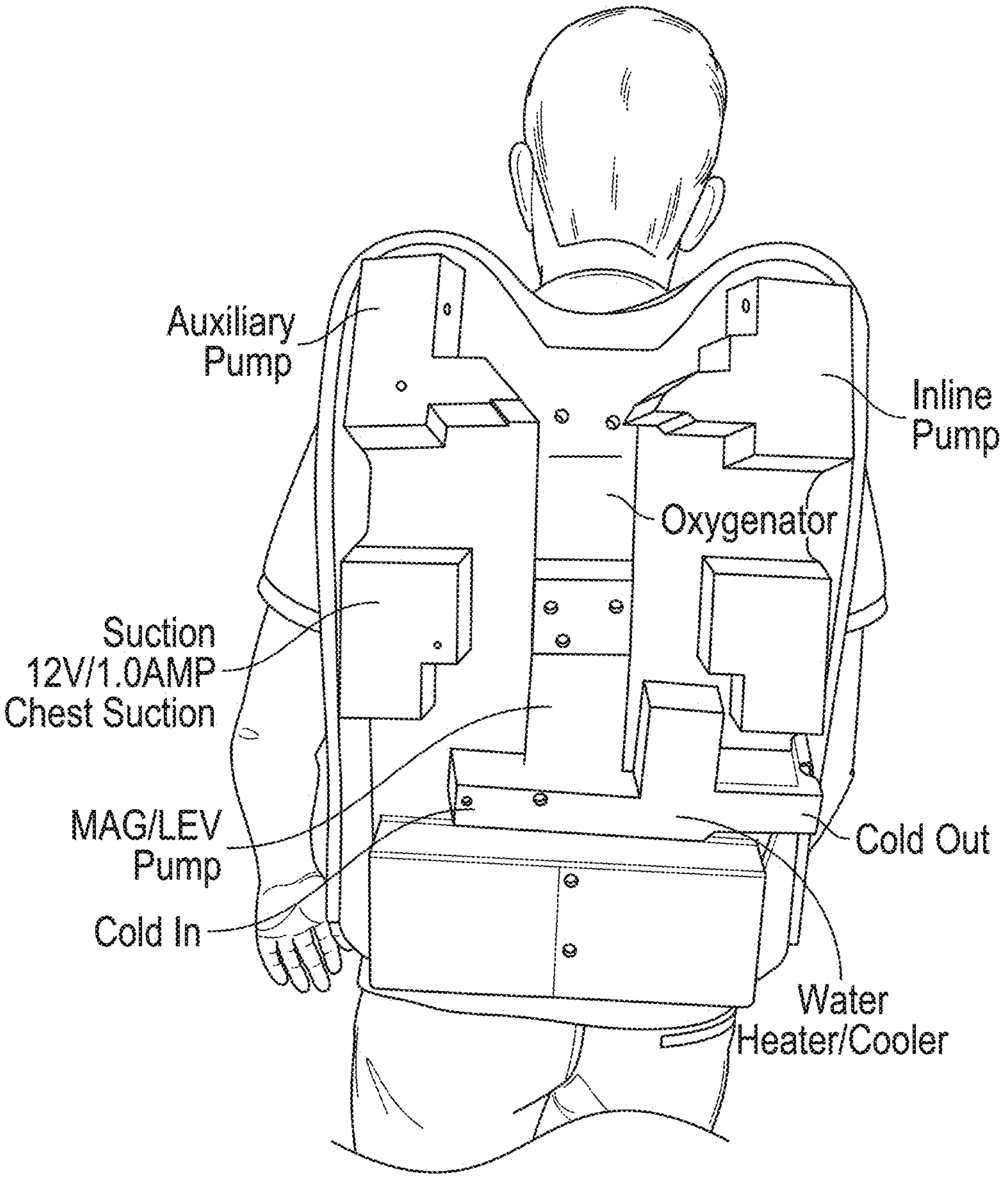
FIG. 4A depicts an example of a system for performing mobile, extracorporeal blood treatment of recovered blood.
Figure 4B:
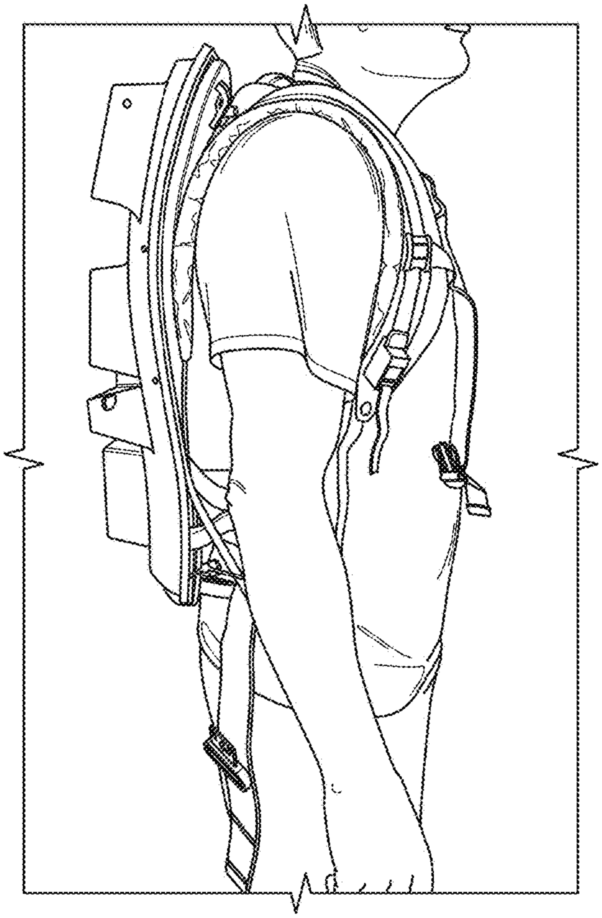
FIG. 4B depicts an example of a system for performing mobile, extracorporeal blood treatment of recovered blood.
Figure 4C:
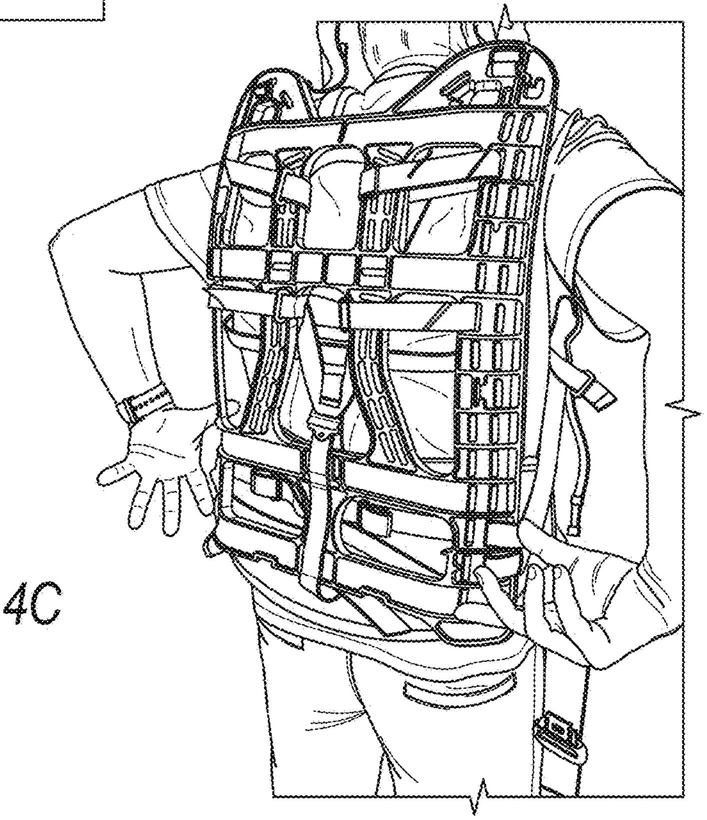
FIG. 4C depicts an example of a system for performing mobile, extracorporeal blood treatment of recovered blood.

FIG. 4A, FIG. 4B, and FIG. 4C depicts another example of a system for performing extracorporeal blood treatment of recovered blood. As shown in FIG. 4A, the system described with respect to FIG. 1A, FIG. 1B, and FIG. 1C as well as the devices described with respect to FIG. 2A, FIG. 2B, and FIG. 2C can be integrated into a mobile trauma management system. For example, such a mobile trauma management system can enable a medic or other technician to assist an injured person in the field, such as away from a hospital operating room setting. For example, the field may be a battlefield, a war zone, a remote area, an ambulance, or a conflict-affected area. In an example, the mobile trauma management system can include a system for blood treatment that is substantially similar to that described with respect to FIG. 1A, FIG. 1B, and FIG. 1C. As shown in FIG. 4A and FIG. 4B, the blood treatment device can be mounted on a carrier such as a backpack including straps. As shown in FIG. 4C the carrier can include a lightweight frame e.g., fabricated with carbon fiber, aluminum, heat-treated thermoplastic polymers, ABS (acrylonitrile butadiene styrene), polystyrene (PS), polycarbonate (PC), or polypropylene (PP). Such a carrier can weigh less than about 10 pounds (lbs) to promote ease of transport. The carrier can optionally also include an internal battery or battery pack operatively engaged with the blood treatment device. As depicted in FIG. 4A, a back panel of the carrier can define recesses sized and shaped to receive components such as an oxygenator, a source of suction, one or more pumps, and a temperature regulation unit. When the mobile trauma management system is removed from the back of the medic or technician, opened, and laid out, the carrier can form a sterile surface from which to perform the procedures described herein.

Figure 5:
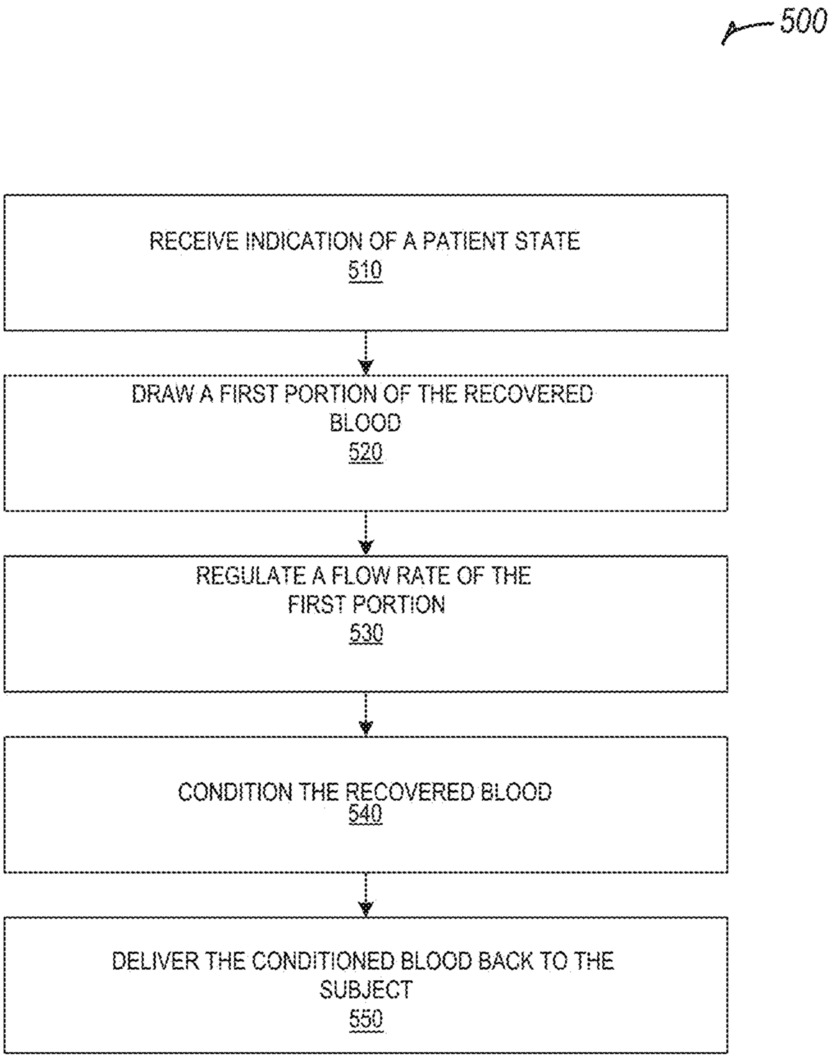
FIG. 5 is a flowchart showing a method for performing extracorporeal blood treatment of recovered blood.

FIG. 5 is a flowchart showing a method for performing extracorporeal blood treatment of recovered blood. The technique 500 can be implemented using one or more devices or systems described herein, such as the system 100 of FIG. 1A, FIG. 1B, and FIG. 1C, the blood treatment device 250 of FIG. 2A and FIG. 2B, etc.

The technique 500 includes an operation 510 to receive an indication of a patient state including a patient having lost greater than 500 milliliters (mL) of blood. Herein, indications and determinations of blood loss include blood "lost" into an internal cavity of the patient, such as an internal bleed, and need not be limited to an actual volume of blood removed from the patient. For example, a patient losing greater than 500 mL of blood can indicate the patient is a trauma patient in need of intervention to avoid hemorrhagic shock. For example, operations 520-550 can be performed conditional upon a determination or receipt of indication that the patient state would otherwise qualify for a massive transfusion protocol.

The technique 500 includes an operation 520 to draw a first portion of the recovered blood from a body cavity of the subject and into a reservoir. For example, a trocar can be placed at the body cavity and connected via a tubing to the reservoir. In an example, the technique can include cutting or enlarging a hole at or near the body cavity to better facilitate access to an internal bleed of the subject. In an example, the reservoir can be sealed relative to an external ambient environment. Here, a negative internal pressure can be applied to the reservoir relative to the external ambient environment, e.g., via a source of suction. The source of suction can be selectively applied or disabled such as to facilitate drainage out of the reservoir when a reservoir valve is opened.

The technique 500 includes an operation 530 to regulate a flow rate of the first portion of the recovered blood. The flow rate can be maintained or regulated at a value greater than 200 milliliters per minute (mL/min). For example, regulating the flow rate can include modulating an inline pump, e.g., between about 1 liter per minute (L/min) and about 10 L/min. In an example, regulating the flow rate can include modifying a flow rate based on an established or adjusted blood treatment operating mode.

The technique 500 includes an operation 540 to condition the recovered blood. For example, conditioning the recovered blood can include reoxygenating hemoglobin (Hb) or removing carbon dioxide ($CO_2$) from the recovered blood. Conditioning the recovered blood can also include controlling a temperature of the recovered blood. In an example, a temperature of the recovered blood can be controlled, e.g., heated, before reoxygenating Hb. In an example, regulating the temperature can include modifying a temperature based on an established or adjusted blood treatment operating mode.

The technique 500 includes an operation to monitor an indication of blood state over time. For example, the indication of blood state can include monitoring a blood volume recovered from the patient over time. The indication of blood state can also include an indication of blood lactate concentration over time, e.g., received from a blood lactate sensor. The indication of blood state can also include an indication of arterial blood gas (ABG) over time, e.g., received from an ABG sensor.

The technique 500 includes an operation 550 to deliver the conditioned, recovered blood back to the subject at least intravenously. The technique 500, in certain blood treatment operating modes, can include delivering the conditioned, recovered blood back to the subject both intravenously and intra-arterially. In an example, an anticoagulant can be administered to the subject prior to the drawing the first portion of the recovered blood from the body cavity of the subject into the reservoir. For example, the blood thinning agent can include heparin, bivalirudin, or argatroban.

In an example, the technique 500 can include establishing or adjusting a blood conditioner operating parameter based on blood state. For example, the blood conditioner operating parameter can be at least one operating parameter of an oxygenator or a temperature regulator. The blood conditioner operating parameter can be established or adjusted based on a monitored indication of blood lactate concentration of the subject over time.

In an example, the technique 500 can include establishing or adjusting a blood treatment operating mode, determined at least in part based on the monitored indication of blood state over time. For example, the blood treatment operating mode can be selected between an assist mode, an acidosis mode, and a controlled preservation mode. For example, in the assist mode, blood can be regulated at a first temperature and reoxygenated blood can be delivered intravenously back to the subject after the reoxygenating Hb. In the acidosis mode, the flow rate of the first portion of the recovered blood can be increased and a second portion of the recovered blood can be received via intravenous cannulation of the subject. In an example, the flow rate of both the first portion and the second portion of the recovered blood can be regulated via the same pump. In the controlled preservation mode, a biological function of the subject can be slowed to help preserve organ tissue. The controlled preservation mode can include cooling the recovered blood toward a second temperature lower than the first temperature before delivering the cooled blood back intra-arterially to the subject. For example, in the controlled preservation mode, an internal body temperature can of the patient can be induced to a temperature between about 10° C. and 20° C. Also, in the controlled preservation mode, controlled hypothermic arrest can be induced in the patient. In an example, the assist mode, the acidosis mode, and the controlled preservation mode of blood treatment can be performed sequentially, such as to escalate a blood treatment protocol based on a declining patient condition. For example, the declining patient condition can be determined based on the measured indication of blood state, such a monitored indication of blood lactate concentration.

Figure 6:
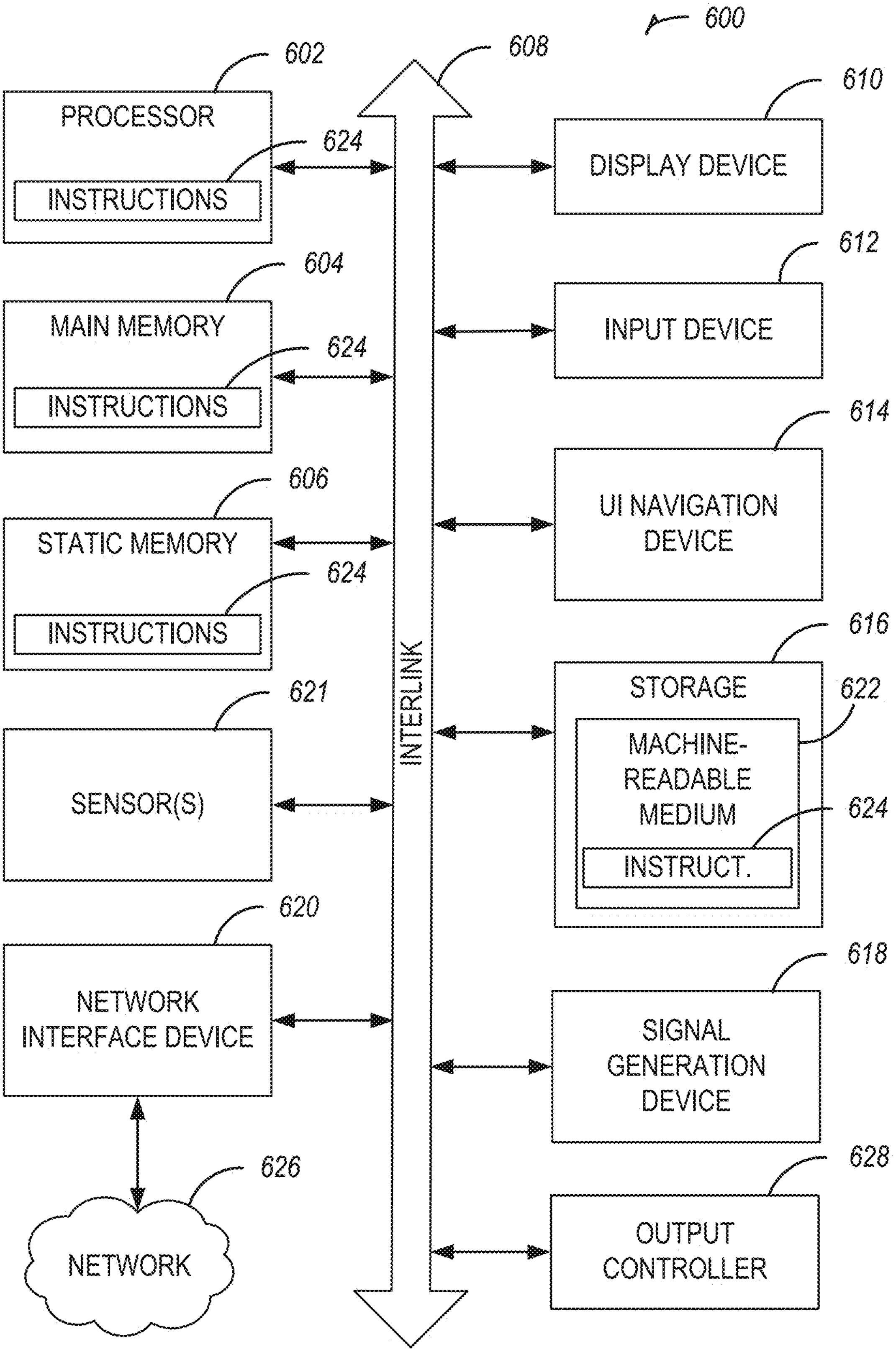
FIG. 6 is a block diagram of an example of a machine.

FIG. 6 illustrates generally an example of a block diagram of a machine 600 upon which any one or more of the techniques (e.g., methodologies) discussed herein may perform in accordance with some examples. In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the execution units or a loading mechanism. Accordingly, the execution units are communicatively coupled to the computer readable medium when the device is operating. In this example, the execution units may be a member of more than one module. For example, under operation, the execution units may be configured by a first set of instructions to implement a first module at one point in time and reconfigured by a second set of instructions to implement a second module.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610, an alphanumeric input device 612 (e.g., a keyboard), and a user interface (UI) navigation device 614 (e.g., a mouse). In an example, the display unit 610, alphanumeric input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or another sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 that is non-transitory on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media. Specific examples of machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

The following, non-limiting examples, detail certain aspects of the present subject matter to solve the challenges and provide the benefits discussed herein, among others.

The above Detailed Description can include references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that can include elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" can include "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that can include elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method for extracorporeal blood treatment of recovered blood, the method comprising:

receiving an indication of a patient state including the patient having lost greater than a first specified threshold value of blood from a body cavity;

drawing, upon receiving the indication, a first portion of the recovered blood from a body cavity of a subject and into a reservoir via a first fluid inlet, the reservoir fluidly sealed relative to an external ambient environment and configured to maintain a negative internal pressure relative to the external ambient environment;

regulating a flow rate of at least the first portion of the recovered blood at a greater rate than a second specified threshold value, received from the first fluid inlet or the reservoir, via an inline pump fluidly coupled to an outlet of the reservoir;

monitoring an indication of blood state over time, the indication of blood state including an indication of blood lactate concentration of at least the first portion of the recovered blood received via at least the first fluid inlet; and conditioning the recovered blood including removing lactate, the conditioning including at least one of reoxygenating hemoglobin (Hb) included in the recovered blood or selectively controlling a temperature of the recovered blood, before at least intravenous delivery back to the subject via at least a first fluid outlet; and delivering the conditioned, recovered blood back to the subject at least intravenously.

2. The method of claim 1, wherein the conditioning is based at least in part on the monitored blood lactate.

3. The method of claim 2, comprising:

establishing or adjusting a blood treatment operating mode that is determined at least in part based on the monitored blood lactate concentration, between at least two of:

an assist mode, including regulating the blood at a first temperature and delivering reoxygenated blood back intravenously to the subject after reoxygenating Hb; and an intermediate mode, including temporarily increasing or intensifying a therapeutic effect provided to the subject via the conditioned, recovered blood and in response to the determination that the lactate concentration is worsening beyond a threshold parameter; and a controlled preservation mode, including temporarily slowing a biological function of the subject to help preserve organ tissue, including cooling the recovered blood toward a second temperature lower than the first temperature before delivering the cooled blood back intraarterially to the subject.

4. The method of claim 3, wherein the blood treatment operating mode is established or adjusted based at least in part on a determination of a lactate concentration at or approaching a threshold value between about 1 millimole per deciliter (mmol/dL) and about 3 mmol/dL.

5. The method of claim 3, wherein establishing or adjusting the blood treatment operating mode as the intermediate mode includes adjusting at least one of a flow rate, temperature, oxygenation, or sweep gas parameter such as to increase the therapeutic effect provided to the subject.

6. The method of claim 3, wherein establishing or adjusting the blood treatment operating mode as the intermediate mode includes regulating the flow rate within a range of about 0.5 liters per minute (L/min) and about 7 L/min.

7. The method of claim 3, wherein establishing or adjusting the blood treatment operating mode as the intermediate mode includes drawing intravenous blood from the subject via an intravenous cannula.

8. The method of claim 3, wherein establishing or adjusting the blood treatment operating mode as the controlled preservation mode includes inducing an internal body temperature of the subject between 10° C. and 20° C. and inducing controlled hypothermic arrest of the subject.

9. The method of claim 1, comprising administering an anticoagulant to the subject prior to the drawing the first portion of the recovered blood from the body cavity of the subject and into the reservoir.

10. The method of claim 1, wherein the first specified threshold value is 500 milliliters.

11. The method of claim 1, wherein the second specified threshold value is 200 milliliters per minute (mL/min).

* * * * *